United States Patent [19]

Ravella et al.

[11] Patent Number: 4,975,164

[45] Date of Patent: Dec. 4, 1990

[54] CONVERSION OF $C_2+$ HYDROCARBONS USING MICROWAVE RADIATION (OP-3515)

[75] Inventors: Alberto Ravella, Sarnia; William J. Murphy, Brights Grove; Biddanda V. Achia, Clearwater, all of Canada

[73] Assignee: Exxon Research and Engineering Company, Florham Park, N.J.

[21] Appl. No.: 457,604

[22] Filed: Dec. 27, 1989

[51] Int. Cl.$^5$ ................................................. C25B 5/00
[52] U.S. Cl. ..................................... 204/156; 204/156; 204/157.43
[58] Field of Search ........................... 204/156, 157.43

[56] References Cited

U.S. PATENT DOCUMENTS 3,308,050 3/1967 Denis .............................. 422/186.03
4,898,748 2/1990 Kruger .................................. 427/38

Primary Examiner—John F. Niebling
Assistant Examiner—Isabelle R. McAndrews
Attorney, Agent, or Firm—John W. Ditsler

[57] ABSTRACT $C_2+$ hydrocarbons can be effectively converted to primarily unsaturated hydrocarbons and hydrogen using microwave radiation in the presence of at least one plasma initiator that is capable of initiating an electric discharge in an electromagnetic field.

30 Claims, No Drawings

CONVERSION OF $C_{2+}$ HYDROCARBONS USING MICROWAVE RADIATION (OP-3515)

BACKGROUND OF THE INVENTION

1. Field of the Invention

This invention relates to a method for converting $C_{2+}$ hydrocarbons to primarily unsaturated hydrocarbons and hydrogen using microwave radiation.

2. Description of the Related Art

Microwave energy has been used to convert methane to other hydrocarbons. For example, U.S. Pat. No. 4,574,038 discloses that methane can be converted to ethylene and hydrogen in a batch process at pressures of from 0.3 to 1 atmosphere by subjecting the methane to microwave radiation in the presence of a metal powder catalyst. Another example of methane conversion using microwave energy is U.S. Pat. No. 3,663,394.

However, neither patent suggests the particular hydrocarbon conversion process described below.

SUMMARY OF THE INVENTION

This invention concerns the synthesis of primarily unsaturated hydrocarbons and hydrogen from a more saturated source. More specifically, $C_{2+}$ hydrocarbons (e.g. $C_2$-$C_4$ saturated hydrocarbons) can be converted to primarily unsaturated hydrocarbons (e.g. acetylene and ethylene) and hydrogen by irradiating the mixture with microwave radiation in the pressure of at least one elongated plasma initiator that is capable of initiating an electric discharge in an electromagnetic field. In a preferred embodiment, molecular hydrogen will be present initially and the plasma initiator will comprise a plurality of elongated metal wire segments arranged in close proximity to one another.

DETAILED DESCRIPTION OF THE INVENTION

This invention requires the presence of $C_{2+}$ hydrocarbon, at least one elongated plasma initiator capable of initiating an electric discharge in an electromagnetic field, and a source of microwave energy.

By "$C_{2+}$ hydrocarbon" or "$C_{2+}$ hydrocarbons" is meant essentially any hydrocarbon containing at least 2 carbon atoms that is in the vapor or gas phase at conversion conditions. The $C_{2+}$ hydrocarbons may be pure (e.g. ethane, propane, butane, pentane, propylene, butylenes, pentenes, mixtures thereof, and the like), a mixture (e.g., light and heavy naphthas, kerosine, light and heavy distillates, gas oils, mixtures thereof, and the like), or both. Non-hydrocarbons (e.g., $CO_2$, $H_2S$ $N_2$, dimethylsulfide, thiophene, etc.) may be present as well.

The plasma initiator may be essentially any material capable of accumulating an electric charge when placed in an electromagnetic field and then dissipating the charge (or initiating an electric discharge), for example, by ionizing a gas environment. This includes metal initiators, non-metal initiators (including semi-conductors), and composites of metal and non-metal initiators. As used herein, "composite" is meant to include mixtures (or combinations) of metals and non-metals. Examples of suitable metal initiators are tungsten, iron, nickel, copper, their alloys, or mixtures thereof. Preferred metal initiators are tungsten, iron, or mixtures thereof. Examples of suitable non-metal initiators include carbon, alumina, manganese dioxide, magnetite, nickel oxide (e.g. NiO), iron oxide (e.g. $Fe_3O_4$), calcium aluminate, cobalt oxide, chromium nitride, iron sulfide (e.g. $FeS_2$, $Fe_{1-x}S$), copper sulfide (e.g. $CuS_2$), or mixtures thereof. Calcium aluminate, carbon, iron oxide, or their mixtures are preferred non-metal initiators, with carbon being particularly preferred. Silica is not a suitable non-metal initiator. However, silica composited with a metal initiator or another non-metal initiator would be a suitable plasma initiator.

Although $C_{2+}$ hydrocarbon conversion can be effected using only one plasma initiator, conversion is enhanced if more than one (e.g., 6 or more) plasma intitiators are used. Preferably, a plurality of plasma initiators are used. Most preferably, the plasma initiator will comprise a plurality of metal wire segments. Each plasma initiator should be of at least a minimum length that is sufficient to initiate an electric discharge when placed in an electromagnetic field. However, the precise minimum length of each initiator may vary with the frequency of the microwave source as well as the geometry of the reaction zone and of the initiator.

If more than one plasma initiator is used, a minimum distance should be maintained between each initiator to facilitate dissipation of the electric charge. However, the minimum distance will vary depending upon the frequency of the microwave source. As an example, the minimum distance should be at least about 0.25 cm, preferably at least about 0.5 cm, for a frequency of 2.45 GHz.

The plasma initiators should be elongated, but may be formed, combined, or bent in any convenient shaped (e.g., straight, helix, spiral, and the like). Preferably, the initiators should be formed such that there are points or sharp edges at the ends or on the surface of the initiators.

The plasma initiators may be stationary within the reaction zone or they may be in motion. The motion can result from the initiators being fluidized by a gas (e.g. the $C_{2+}$ hydrocarbon feedstock) or by other means (e.g. an external magnetic field gradient).

The frequency of the microwave source can vary broadly. Typically, the microwave energy will have a frequency of at least 0.3 GHz, with frequencies centered around 0.915, 2.45, 5.80, or 22.0 GHz being presently preferred in North America; particularly frequencies centered around 0.915, 2.45, or 5.80 GHz; especially frequencies centered around 0.915 or 2.45 GHz.

The microwave energy used in this invention may be continuous or pulsed. If pulsed, the duration of on-time pulses can vary broadly, but typically will range from about 1 nanosecond to about 20 seconds, preferably from about 1 millisecond to about 10 seconds, and most preferably from about 0.01 to about 0.2 seconds. The duration of off-time rests can vary broadly as well, but typically will range from about 1 nanosecond to about 100 seconds, preferably from about 0.003 to about 60 seconds, and most preferably from about 0.03 to about 5 seconds.

Hydrogen should also be present in the reaction zone to maintain the activity of the plasma initiators for $C_{2+}$ hydrocarbon conversion. The amount of hydrogen in the reaction zone during conversion should be sufficient to maintain a carbon (based on carbon in the $C_{2+}$ hydrocarbons) to hydrogen weight ratio less than 6:1, preferably less than 4:1, more preferably less than 3:1, and most preferably less than 1.5:1. Although some $C_{2+}$ hydrocarbon conversion may occur at weight ratios of 6:1 or more, greater conversion will be obtained at lower weight ratios because hydrogen tends to reduce or inhibit the formation of carbonaceous deposits on the plasma initiators. While not wishing to be bound by any particular theory, it is believed that at higher weight ratios, greater amounts of carbonaceous deposits accumulate on the initiators and inhibit their ability to ionize the gas environment.

Although extraneous hydrogen need not be added, if a sufficient amount of hydrogen is not present initially in the reaction zone, the initiators will deactivate until a sufficient amount of hydrogen is present (or has accumulated, for example, by recycling the hydrogen formed during conversion) to retard deactivation and maintain the weight ratio at a level that will stabilize the $C_{2+}$ hydrocarbon conversion at a particular level. This so-called induction period results in an initial loss of initiator activity and, hence, a lower lever of $C_{2+}$ hydrocarbon conversion than if hydrogen had been present initially. To avoid this undesirable loss of conversion, it is preferred to add extraneous hydrogen to the reaction zone initially to minimize or prevent the initial loss of initiator activity and $C_{2+}$ hydrocarbon conversion. This extraneous hydrogen may be pure or in a mixture with other gases (e.g. as from a naphtha reformer) and may be added to the reaction zone separately or in mixture with the $C_{2+}$ hydrocarbons.

This invention can be practiced at any convenient temperature and pressure, including ambient conditions, provided the $C_{2+}$ hydrocarbons are in the vapor or gas phase during conversion. However, the relative amounts of acetylene and ethylene formed will vary with pressure, with a greater amount of ethylene being formed at elevated pressures (i.e., pressures greater than atmospheric). In addition to acetylene and ethylene, this invention also contemplates the formation of aromatic compounds such as benzene, alkyl benzenes, xylenes, and the like.

This invention will be further understood by reference to the following Examples which are not intended to restrict the scope of the appended claims.

EXAMPLE 1

Conversion of Butane Using Continuous Microwave Radiation

A butane/hydrogen mixture (1:16 mole ratio, equivalent to a 1.5:1 carbon to hydrogen weight ratio) flowing at 85 ml/minutes (5 milliliters/minute butane, 80 ml/min hydrogen) at atmospheric pressure was contacted with 0.37 g of a straight tungsten wire (approximately 0.76 mm in diameter cut into about 47 mm lengths) in a reactor of a straight piece of quartz tubing (7 mm in internal diameter). The part of the tube containing the wire was inserted in a WR430 microwave waveguide and positioned approximately one quarter waveguide wavelength from a short circuit plate. The reactor was then irradiated with continuous microwave radiation centered at 2:45 GHz frequency, with an average power between 10 and 20 watts. Butane conversion was calculated to be 46.8% using the following equation:

% Butane Conversion =

$$\left[1 - \frac{\text{wt. \% butane in the products}}{\text{wt. \% butane in the feed}}\right] \times 100$$

Based on an average of four different samples taken after about 140 minutes (analyzed by gas chromatography), the primary products were 17.9 wt.% acetylene, 12.3 wt.% ethylene, and 0.5 wt.% hydrogen. About 3.5 wt.% $C_3$'s and 0.9 wt.% ethane were also present.

EXAMPLE 2

Product Selectivity From Converting Butane Versus From Converting Methane

Table 1 below compares the results from Example 1 with data obtained from processing methane in the same apparatus at similar conditions (power between 10 and 20 watts and a carbon to hydrogen weight ratio of 1.5:1). Butane (or methane) conversion was calculated using the equation in Example 1.

TABLE 1

| Flow Rate, (ml/min) | | | Pressure, psig | Conversion, % | Acetylene/ Ethylene, weight ratio |
|---|---|---|---|---|---|
| $H_2$ | $C_4H_{10}$ | $CH_4$ | | | |
| 80 | 5 | — | 0 | 46.8 | 1.5 |
| 60 | — | 15 | 0 | 56.1 | 7.0 |
| 60 | — | 15 | 46 | 41.2 | 1.5 |

The data in Table 1 show the under similar operating conditions, conversion of butane results in a higher selectivity for ethylene than is obtained with methane conversion. This data also show that operating pressure has a significant influence on ethylene selectivity.

EXAMPLE 3

Conversion of Butane using Pulsed Microwave Radiation

Example 1 was repeated except that the power was applied as pulsed energy having a duty cycle of 0.11 seconds on and 0.09 seconds off. The average power was 12 watts. Based on an average of four different samples after about 210 minutes (using gas chromatography), butane was converted (42.8%) to 9.6 wt.% methane, 10.6 wt.% ethylene, 10.4 wt.% acetylene, 0.8 wt.% ethane, 3.3 wt.% $C_3$'s, and 2.3 wt.% hydrogen.

EXAMPLE 4

Conversion of Ethane Using Continuous Microwave Radiation

Using the procedure of Example 1 (except that the power was 8 watts), ethane was converted (60.3%) to 10.4 wt.% methane, 17 wt.% ethylene, 25.8 wt.% acetylene, 1.2 wt.% $C_3$'s, and 5.4 wt.% hydrogen. These results were based on gas chromatographic analysis of about four different samples after about 170 minutes.

What is claimed is:

1. A method converting a $C_{2+}$ hydrocarbon to acetylene, ethylene, and hydrogen which comprises:
   (a) introducing the $C_{2+}$ hydrocarbon into a reaction zone that contains at least one plasma initiator capable of initiating an electric discharge in an electromagnetic field, and
   (b) subjecting the $C_{2+}$ hydrocarbon and plasma initiator to microwave radiation for a period of time sufficient to convert at least a portion of the $C_{2+}$ hydrocarbon to acetylene, ethylene, and hydrogen.

2. The method of claim 1 wherein the plasma initiator is a metal.

3. The method of claim 2 wherein the metal is tungsten, iron, nickel, copper, their alloys, or mixtures thereof.

4. The method of claim 3 wherein the metal is tungsten or iron.

5. The method of claim 1 wherein the plasma initiator is a non-metal other than silica.

6. The method of claim 5 wherein the non-metal is calcium aluminate, carbon, iron oxide, or mixtures thereof.

7. The method of claim 1 wherein the plasma initiator is a composite of a metal initiator and a non-metal initiator.

8. The method of claim 1 wherein the weight ratio of carbon in the $C_2+$ hydrocarbon to hydrogen is less than 6:1 during conversion.

9. The method of claim 1 wherein a plurality of plasma initiators are present in the reaction zone.

10. The method of claim 1 wherein the frequency of the microwave radiation is at least 0.3 GHz.

11. The method of claim 10 wherein the frequency of the microwave radiation is centered around 0.915, 2.45, or 5.8 GHz.

12. The method of claim 1 wherein the $C_2+$ hydrocarbon comprises ethane.

13. The method of claim 1 wherein the $C_2+$ hydrocarbon comprises butane.

14. A method for converting a $C_2+$ hydrocarbon to acetylene, ethylene, and hydrogen which comprises:
   (a) introducing the $C_2+$ hydrocarbon into a reaction zone which contains a plurality of plasma initiators capable of initiating an electric discharge in an electromagnetic field, and
   (b) subjecting the $C_2+$ hydrocarbon and plasma initiators to microwave radiation having a frequency of at least 0.3 GHz for a period of time sufficient to convert at least a portion of the $C_2+$ hydrocarbon to acetylene, ethylene, and hydrogen, wherein the weight ratio of carbon in the $C_2+$ hydrocarbon to hydrogen is less than 6:1 during conversion.

15. The method of claim 14 wherein the pressure in the reaction zone is greater than atmospheric pressure.

16. The method of claim 15 wherein the $C_2+$ hydrocarbon is converted to primarily ethylene and hydrogen.

17. The method of claim 14 wherein at least one plasma initiator is a metal.

18. The method of claim 17 wherein the metal is tungsten, iron, nickel, copper, their alloys, or mixtures thereof.

19. The method of claim 18 wherein the metal comprises iron.

20. The method of claim 14 wherein at least one plasma initiator is a non-metal other than silica.

21. The method of claim 20 wherein the non-metal is calcium aluminate, carbon, iron oxide, or mixtures thereof.

22. The method of claim 14 wherein at least one plasma initiator is a composite of a metal initiator and a non-metal initiator.

23. The method of claim 14 wherein the frequency of the microwave radiation is centered around 0.915, 2.45, or 5.8 GHz.

24. The method of claim 14 wherein the microwave radiation is pulsed.

25. The method of claim 24 wherein the duration of on-time pulses ranges from 1 millisecond to about 10 seconds and the duration of off-time pulses ranges from about 0.003 to about 60 seconds.

26. The method of claim 14 wherein the weight ratio of carbon in the $C_2+$ hydrocarbon to hydrogen is less than 3:1.

27. The method of claim 14 wherein the $C_2+$ hydrocarbon comprises ethane.

28. The method of claim 14 wherein the $C_2+$ hydrocarbon comprises butane.

29. The method of claim 14 wherein at least one aromatic compound is formed during the $C_2+$ hydrocarbon conversion.

30. A method for converting a $C_2+$ hydrocarbon to primarily ethylene and hydrogen which comprises:
   (a) introducing the $C_2+$ hydrocarbon into a reaction zone that contains at least one plasma initiator capable of initiating an electric discharge in an electromagnetic field, and
   (b) subjecting the $C_2+$ hydrocarbon and plasma initiator to microwave radiation for a period of time sufficient to convert at least a portion of the $C_2+$ hydrocarbon to primarily ethylene and hydrogen.

* * * * *